(12) United States Patent
Taskinen et al.

(10) Patent No.: US 9,955,933 B2
(45) Date of Patent: *May 1, 2018

(54) ARRANGEMENT FOR CONTROLLING IMAGE PLATE AND ITS IMAGE INFORMATION AND A METHOD FOR CONTROLLING THE ARRANGEMENT

(71) Applicant: PaloDEx Group Oy, Tuusula (FI)

(72) Inventors: Jari Taskinen, Tuusula (FI); Mika Anttila, Espoo (FI); Timo Klemola, Kerava (FI)

(73) Assignee: PaloDEx Group Oy, Tuusula (FI)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/588,070

(22) Filed: May 5, 2017

(65) Prior Publication Data

US 2017/0238891 A1    Aug. 24, 2017

Related U.S. Application Data

(63) Continuation of application No. 13/258,311, filed as application No. PCT/FI2010/050215 on Mar. 22, 2010, now Pat. No. 9,678,420.

(30) Foreign Application Priority Data

Mar. 23, 2009  (FI) ...................................... 20095299

(51) Int. Cl.
*A61B 6/00* (2006.01)
*G06K 7/10* (2006.01)
*A61B 6/14* (2006.01)

(52) U.S. Cl.
CPC ........ *A61B 6/4494* (2013.01); *G06K 7/10366* (2013.01); *A61B 6/145* (2013.01)

(58) Field of Classification Search
CPC ................................ A61B 6/547; G03B 42/08
See application file for complete search history.

(56) References Cited

U.S. PATENT DOCUMENTS

| 6,271,536 B1 | 8/2001 | Buytaert et al. |
| 7,573,034 B2 | 8/2009 | Heath et al. |
| 8,471,684 B2 | 6/2013 | Wong |

(Continued)

FOREIGN PATENT DOCUMENTS

| EP | 0727696 A1 | 8/1996 |
| EP | 1251683 A1 | 10/2002 |

(Continued)

OTHER PUBLICATIONS

Decision of Rejection for Japanese Patent Application No. 2012-501329 dated Sep. 16, 2014.

(Continued)

*Primary Examiner* — Nabil Syed
(74) *Attorney, Agent, or Firm* — Andrus Intellectual Property Law, LLP (57) ABSTRACT

A medical imaging system comprises at least an image plate, X-ray device for producing an image of an object on said image plate, and a reading device for reading image information held by the image plate. In connection with the image plate there is a tag containing information for controlling the arrangement in such a manner that when the arrangement has read the information in the tag the arrangement is adapted to perform at least one operation controlled by the information read.

20 Claims, 1 Drawing Sheet

(56) References Cited

U.S. PATENT DOCUMENTS

| | | |
|---|---|---|
| 2005/0134936 A1 | 6/2005 | Haug et al. |
| 2005/0156125 A1 | 7/2005 | Rimsa et al. |
| 2005/0180566 A1 | 8/2005 | Ryal |
| 2005/0236593 A1 | 10/2005 | Ivo |
| 2006/0261296 A1 | 11/2006 | Heath et al. |
| 2008/0237478 A1 | 10/2008 | Kito |
| 2009/0026392 A1 | 1/2009 | Yoshimi et al. |
| 2009/0103796 A1 | 4/2009 | Akagi et al. |
| 2009/0212107 A1 | 8/2009 | Crucs et al. |

FOREIGN PATENT DOCUMENTS

| | | |
|---|---|---|
| JP | S63253348 | 10/1988 |
| JP | 2004-295850 A | 10/2004 |
| JP | 2005-257634 A | 9/2005 |
| JP | 2005-275310 A | 10/2005 |
| JP | 2007-249939 A | 9/2007 |
| JP | 2007334027 | 12/2007 |
| JP | 2008-076585 A | 4/2008 |
| JP | 2008-246102 A | 10/2008 |
| JP | 2009-080032 A | 4/2009 |
| NO | 2005055007 A2 | 6/2005 |
| NO | 2006060238 A2 | 6/2006 |
| NO | 2006129498 A1 | 12/2006 |
| WO | 2008111355 A1 | 9/2008 |

OTHER PUBLICATIONS

Finish Office Action in corresponding Finnish Application No. 20095299 dated Mar. 1, 2013.

Notification of Fourth Office Action issued by the Chinese Patent Office dated Apr. 19, 2015 in corresponding Chinese Patent Application No. 20108002095.9.

Notification of Reason for Refusal issued by the Japanese Patent Office dated Sep. 5, 2013 in corresponding Japanese Patent Application No. 2012-501329.

Notification of Transmittal of the International Search Report and the Written Opinion of the International Searching Authority, or the Declaration for parent application PCT/FI2010/050215, dated Jul. 6, 2010.

ARRANGEMENT FOR CONTROLLING IMAGE PLATE AND ITS IMAGE INFORMATION AND A METHOD FOR CONTROLLING THE ARRANGEMENT

The invention relates to medical imaging, comprising an image plate, an X-ray device which generates X-rays for producing on said image plate an image of an object examined, and a reading device for reading image information contained in the image plate. In particular, the invention relates to an arrangement, template and method for controlling image plates and their image information in medical imaging, and a method for controlling the arrangement. The invention also relates to an image plate packing means to implement said method.

PRIOR ART

In modern medical imaging, images of objects are taken on image plates from which the image information is read by means of a reading device. One image plate can typically be used several times and the image information contained therein is reset between imaging operations. It is obvious that many different persons will use a given image plate during its life span and that an image plate will contain images of several patients and even different body parts of different patients.

A problem therefore is that used image plates may become mixed up. For instance, image information read from an image plate may end up in the hands of a wrong doctor or it may become associated with a wrong patient or, in the case of a series of image plates where the mutual order of plates is important, the plates may get into a wrong order so that it may even become practically impossible to reconstruct an image consisting of image information from a plurality of image plates. In some circumstances the image information of an image plate cannot later be associated with the correct patient.

A known solution is to reserve the reading device in advance to a given doctor and read the image information contained by the image plates immediately after the reservation so that the image information will end up in the database of said doctor, for example. However, this has the drawback that when the reservation time of the reading device is not long enough to start reading the image plates, someone else may make a simultaneous reservation and thus image information of the first reserver may end up in a wrong place or even to a wrong patient. Another drawback is that in a series of multiple image plates, the plates must be read in a particular order, and if e.g. a human error is made, that order may become confused.

SUMMARY

An object of the invention is to provide a solution mitigating the above-mentioned disadvantages related to the prior art. One object of the invention is to solve the question of how to ascertain that image information contained in image plates ends up in the correct place, e.g. to the party that took and/or will interpret the image, e.g. a doctor, and/or in a mass storage device so that said image information can be associated with the appropriate object e.g. the correct patient or the doctor who took or will interpret the image.

Another object of the invention is to make possible the insertion of image plates in the reading device and the reading of image plates in an arbitrary order also in conjunction with an image series consisting of a plurality of image plates, each image plate in the image series having a certain position with respect to other image plates in the image series, the anatomy of the object examined, and/or the imaging equipment, for example.

The objects of the invention are achieved by an arrangement according to claim 1, method according to claim 20, reading device according to claim 23, and X-ray device according to claim 25.

An arrangement according to the invention is characterised by that which is specified in the arrangement claim 1.

Methods according to the invention are characterised by that which is specified in the method claim 20.

A reading device according to the invention is characterised by that which is specified in claim 23 directed to a reading device.

An X-ray device according to the invention is characterised by that which is specified in claim 25 directed to an X-ray device.

In one embodiment, there is in connection with an image plate intended for medical imaging or in connection with a transport and/or protection means associated with said image plate, a tag which can be remotely written to and/or read and which contains information for controlling the arrangement in such a manner that when the arrangement has read the information in the tag the arrangement is adapted to perform at least one operation controlled by the information read.

In one embodiment, the information in the tag is used for controlling the arrangement in such a manner that the image information contained in the image plate is delivered to a party specified by information read from the tag, e.g. to the party that took and/or will interpret the image, image processing means in a given room, or to a certain doctor. The image information may also be delivered to a mass storage device so that said image information can be associated with that particular imaging event and/or person involved. Controlled by the information in the tag, a folder or database, for instance, can be created in the mass storage device for the object in question to store the image data. The image data may also be transferred, controlled by the information in the tag, to an existing folder in the mass storage device, e.g. a folder of the doctor who will interpret the images or who took the images.

In one embodiment, the arrangement, having read the tag, is adapted to read from database means information associated with the tag, and to perform an operation controlled by that information. It should be noted that the above-described embodiment for controlling the arrangement can be used as an alternative for embodiments in which information read from the tag is used as such for controlling the arrangement.

In one embodiment, the information that is written in the image plate tag or the information associated with the tag in the database means comprises information related to the position of the image plate in the imaging, e.g. position information indicating the position of the image plate in the imaging operation with respect to the anatomy of the object examined, other image plates used in the operation, and/or imaging equipment. The position information can be written during the imaging operation, for instance. In another embodiment of the invention the arrangement is adapted to deliver the image information, e.g. in connection with a series of multiple images, to the position in the series of images read, as indicated by the position information, at which the image plate was used in the imaging operation. Similarly, the arrangement may also deliver the image information of an individual image plate to a location in a model representing the anatomy of a patient, which location was used for the image plate in the imaging operation. Thus, for example, image information of an upper left canine tooth will be delivered to a location representing the upper left canine tooth in an image series template for at least part of the teeth of the patient.

A tag used in conjunction with an image plate and/or its transport and/or protection means can be implemented with an arrangement based on short-range radio, e.g. RFID, Bluetooth, Wlan, Wusb, Zigbee or Wibree.

In one embodiment of the invention, information may be directly written to the tag to control the arrangement. In another embodiment, the tag may comprise a code (ID) identifying the tag so that control information for controlling the arrangement can be stored e.g. in a database means separate from the tag, to be associated with the ID of the tag. In that case the control of the arrangement may be implemented e.g. such that first it is read the ID of the tag, then from the database means the control information associated with the ID, e.g. a control command for storing the image information of an image plate associated with the ID in the appropriate location.

In an embodiment in which the tag comprises an ID, the tag may also be implemented with read-only tags, e.g. optically-read codes, barcodes, 2D barcodes, alphanumeric characters or other readable codes known to a person skilled in the art.

In one embodiment, the tag contains exposure information indicating that the image plate with which the tag is associated contains image information and the arrangement is adapted to activate, based on the reading of said exposure information, an image plate reading device, for example. Furthermore, in one embodiment, having read or reset the image information the arrangement is adapted to alter the exposure information in the tag to indicate that the image information has been read and/or said image plate does not contain image information.

In one embodiment of the invention the arrangement can be controlled also by controlling the image plates already during the imaging operation. For instance, a place can be reserved for an image plate on a separate template, which place can be identified with respect to the anatomy of the object examined, other image plates used in the imaging operation, and/or imaging equipment. Identification information, e.g. position information, associated with said place to be identified is produced and delivered so that said image plate can be associated with said place at a later stage.

In one embodiment, identification information, e.g. position information, associated with said place of the image plate on the template is written to the tag of the image plate. In another embodiment, the ID of the tag of said image plate is read first and then the identification information of the tag and the identification information, e.g. position information, associated with the place of the image plate on the template are delivered to a database means in such a manner that they can be associated with each other.

In one embodiment, a reader means in connection with an X-ray device reads from the tag of an image plate the position information of the image plate with respect to the anatomy of the object examined and if, according to the position information read from the tag, the image plate is incorrectly positioned in the imaging operation, a notification is given about it and/or the imaging operation is interrupted.

In one embodiment, position information in the tag or in the database means for an image plate is compared with the position of the image plate on said template and an indication for an incorrect position on the template is given if the position information associated with the image plate does not match with the position information corresponding to the position at which the image plate is placed on the template.

In one embodiment of the invention, information about an infectious disease of a patient, for example, could be included in the patient data and/or in the image plate tag. Said information about an infectious disease of a patient can be used for controlling the operation of the arrangement, e.g. by disallowing the interruption of the cleaning of an image plate containing an image of a patient indicated to have an infectious disease, e.g. for the scanning of the image plate, which is possible if the image plate does not include said information. Such information may also be some other predetermined information. Furthermore, the arrangement can be implemented such that it automatically actuates the cleaning of a reading device based on the infectious disease information or some other similar information. Additionally, if the reading device or some other component of the arrangement comprises parts to be cleaned separately, the arrangement can be made such that it prompts the user to clean and/or replace such parts after the imaging of a patient indicated to have an infectious disease.

Furthermore, in one embodiment of the invention, image plates are equipped with image plate transport and/or protection means so that position information associated with an image plate is printed out so as to be attachable onto the image plate and/or its transport and/or protection means and/or said position information associated with the image plate is written to the image plate tag and/or database means where it can be associated with the image plate, wherein the position information indicates the position of the image plate relative to the anatomy of the object examined, other image plates used in the imaging operation, and/or imaging equipment. Equipping of image plates with image plate transport and/or protection means can be done using the packing means described in this document, for example.

In one embodiment of the invention the image plate reading device is adapted to read control information associated with the tag of the image plate and/or its transport and/or protection means and/or the ID of the tag on some other device, and to perform at least one operation controlled by said information read.

In addition, in another embodiment of the invention an X-ray device intended for exposing image information onto an image plate or some other device in connection therewith is adapted to read and/or write control information associated with the tag of the image plate and/or its transport and/or protection means and/or the ID of the tag on some other device, and to perform at least one operation controlled by said information read. The control information may indicate that the image plate is faulty or already contains image information, for example.

The invention has considerable advantages. For example, by means of the image plate tag the image plates can be configured for a particular room, doctor and/or patient or they can be associated with position information relating to the position of image plates in the imaging operation so that the image information of image plates will always be correctly targeted, either to the correct party or at the correct anatomical spot in a template representing e.g. the teeth or some other anatomical part of the patient.

The invention further makes possible that image plates, e.g. in connection with series of multiple images, can be fed into a reading device and read in a completely arbitrary order, and the arrangement can associate the information of the image plates with positions corresponding to those of the image plates in the imaging operation, e.g. on a template representing an anatomical position related to the image series.

Furthermore, the hygiene of the reading device, for example, can be improved when the tag can indicate that the image plate contains image information so that the reading device can be made to automatically become activated without a touch or with a minimal touch when an image plate containing image information is brought in the vicinity of the reading device. Thus, persons involved in the read operation need not physically touch the reading device, minimizing the spreading of infectious diseases.

In addition, the hygiene, efficiency and user-friendliness of the arrangement can be improved when essential information about the patient, e.g. information about an infectious disease or the like, can be used e.g. to control the cleaning of an image plate and/or prompt the user to clean or replace relevant components in the reading device. This way, a lower hygiene level can be applied in the arrangement in normal conditions, and a raised hygiene level can be applied when the patient is known to have an infectious disease, without the user having to see to it especially.

Furthermore, a particular image plate, e.g. an image plate comprising image information, a faulty image plate, an already-read image plate or an image plate with reset image information, can be identified e.g. from a pile of several image plates by means of the image plate tag, where the tag indicates the faultiness of the image plate or tells whether the image plate is empty or whether it holds image information. The identification can be implemented e.g. in such a manner that having read the information in the tag, or information associated with the ID of the tag in a database means, a component in the arrangement, say a reading device, X-ray device or some other device, will generate an audible and/or visible indication. Alternatively or additionally, a display device is connected with the arrangement, e.g. with the reading device or X-ray device, for showing said image plate information to the user. In one embodiment, the reading device, having noticed a faulty image plate, may leave the image plate in the insertion aperture or exit aperture or plate collector and indicate in some of the manners described above that the image plate is faulty and prompt the user to remove it.

Based on image plate tags a reading device may e.g. indicate the number of read, faultless and reset image plates in the plate collector, as well as the nature of information in the image plates located in the vicinity of the reading device. The information may be read direct from the tag or, alternatively, from a database containing the tag ID.

Advantageous embodiments of the invention are presented in the dependent claims.

DESCRIPTION OF DRAWINGS

Advantageous embodiments of the invention will be described below a little more closely, referring to the accompanying drawings in which.

DETAILED DESCRIPTION OF DRAWINGS

Figures 1, 2, 3:
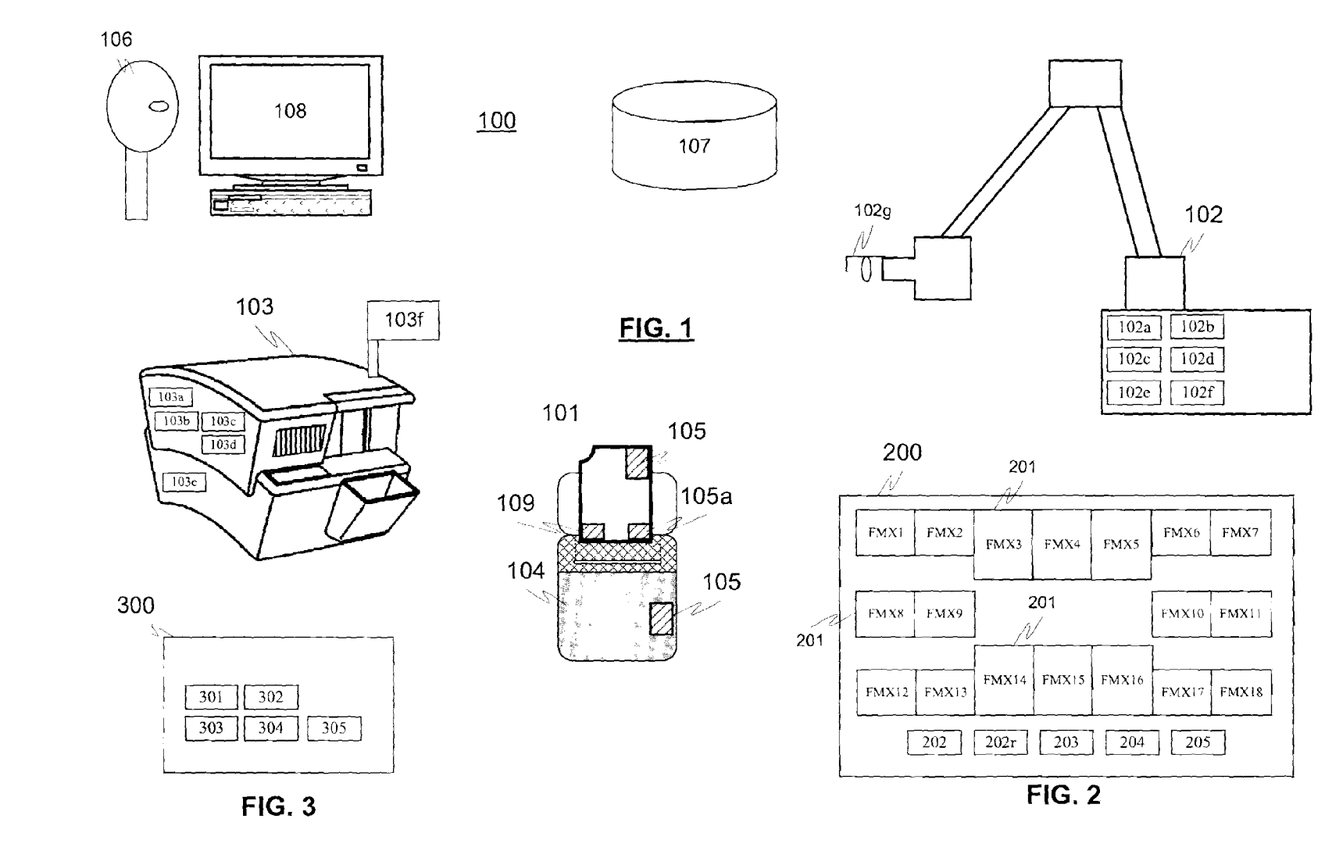
FIG. 1 shows an arrangement for controlling a medical imaging system in accordance with an embodiment of the invention.
FIG. 2 shows a template for managing image plates and image information contained in image plates and thereby controlling a medical imaging system in accordance with an embodiment of the invention.
FIG. 3 shows a packing means for providing image plates with image plate transport and/or protection means and thereby controlling a medical imaging system in accordance with an embodiment of the invention.

FIG. 1 shows an arrangement 100 for controlling a medical imaging system in accordance with an embodiment of the invention, where the arrangement 100 comprises at least an image plate 101, X-ray device 102 for producing an image of an object on said image plate, and a reading device 103 for reading image information held by the image plate. The X-ray device 102 may also comprise an image plate holder 102g.

In one embodiment of the invention, there is in connection with the image plate 101 or in connection with a transport and/or protection 104 means associated with said image plate a tag 105 which can be remotely written to and/or read and which contains information for controlling the system in such a manner that when the system has read the information in the tag the system is adapted to perform at least one operation controlled by the information read. The protection means 104 may comprise a shielding pouch, cassette or some other protective device.

In one embodiment, the reading device 103 comprises a means 103a adapted to deliver the image information read by the reading device to a destination indicated by control information read from the tag, e.g. to the party 106 that took and/or will interpret the image, and/or to a mass storage device 107 so that said image information can be associated with the object of the imaging and/or the person involved in the imaging.

For example, information could be stored in the tag during the imaging or prior to it with respect to the target where the image information contained in the image plate is to be stored. The target may be e.g. a file path or a personal file folder of a doctor or patient, or a database.

Position information may also be stored in the tag during the imaging, for example, where the position information indicates the position of the image plate in the imaging operation e.g. with respect to the anatomy of the object examined, other image plates used in the imaging, and/or imaging equipment. In intra-oral imaging, for instance, the position information may indicate that the image information contained in the image plate relates to an image taken of the upper left canine tooth. Then, the reading means 103a in the reading device 103 is adapted to read the position information and together with the means 103b to deliver the position information to a position corresponding to the upper left canine tooth on a template representing the teeth of a patient or at least attach the information related to said position to the image information read from the image plate and sent forward. The reading device may store the image information in a database means 107 together with the position information, for example. It should be noted that together with the image information also other information can be stored in the database means, e.g. imaging parameters and/or patient information.

This has the advantage that in a series of multiple image plates the image information of each individual image plate can be delivered to that particular position in the image series which was used in the imaging and which is indicated by the information read from tag. Then the image plates containing image information need not be read in a particular order because the reading device can arrange the image information in the correct order with respect to the position information indicated by the tag.

Furthermore, the reading device 103 may comprise a means 103c for writing information to an image plate tag, and also a means 103d for estimating the condition of an image plate, wherein the writing means 103c is adapted to e.g. write to the image plate tag information generated by the means 103c relating to the condition of an image plate. Thus it is possible to write to the image plate tag a piece of information indicating the faultiness of the plate, for instance, so that subsequent devices will also know that it is faulty.

In one embodiment of the invention there is a means 102a in conjunction with the X-ray device 102, for example, said means being adapted to write to the image plate tag during the imaging that said image plate contains image information. In addition, there may be a means 102b in conjunction with the X-ray device 102 for reading an image plate tag, said means being adapted to read information in the tag and, together with the means 102c, for example, produce an indication when an attempt is made to use an image plate which already contains image information according to its tag.

There may also be a means 102d in conjunction with the X-ray device 102, adapted to indicate e.g. the faultiness of an image plate after the means 102b has read from the tag information concerning the condition of the image plate. Faultiness of an image plate and possibly also the fact that the image plate already holds image information can be indicated using an audible and/or visible indication or by the X-ray device refusing to start up or expose the plate. In one embodiment, there is a display in conjunction with the X-ray device for indicating said information to the user.

In one embodiment of the invention the functions of the reading device 103 can be controlled on the basis of information read from the tag by the means 103a. Said means 103a may read from the image plate tag e.g. that an image plate brought in the vicinity of the reading device contains image information, whereby a means 103e is adapted to activate the image plate reading device, e.g. to turn the reading device from inactive mode to active mode. In one embodiment, the reading device 103 may also comprise a display 103f adapted to show information relating to a tag of an image plate controlled by the information in the tag. In another embodiment, the tag may also contain information related to the operator, e.g. a doctor or nurse, of the image plate associated with the tag, whereby the reading device may be adapted to show, through the display means 103f, information associated with the operator. This way it is possible, among other things, to detect inexperienced operators so that more detailed and thorough information can be displayed on the display means for them than to more experienced users.

In one embodiment, the reading device 103 is adapted to write, using its writing means 103c, information into an image plate tag, which information indicates that the image information contained in the image plate has been read and/or the image plate no longer contains image information.

In one embodiment of the invention, an image plate tag may comprise an ID which identifies the tag. In that case a database means 107 may comprise information associated with said ID so that system control information which relates to the image plate can be stored in the database means 107 in association with said ID of the tag. Control information written to the tag in accordance with embodiments described above can in this embodiment be written to the database means in association with the ID of the tag so that imaging system components may read, based on the ID of the tag, system control information from the database means for controlling the system in the various stages of image plate processing.

The ID of the tag of an image plate may be e.g. #123, whereby it is possible during the imaging, for example, to store in the database means system control information relating to the ID in question. Thus, for example, the reading device 103 may read from the image plate tag the ID of the tag and then associated system control information from the database means 107. Then, the reading device 103 is adapted to deliver, on the basis of the control information read from the database means, the image information of an image plate to a correct location e.g. a file folder in a similar fashion as in an embodiment described earlier in this document where the location information is read direct from the tag.

Additionally, the reading device 103 and/or X-ray device 102 may write into the database means 107 system control information associated with the image plate and/or imaging event so that the control information can be associated with that particular tag and further with the image plate associated with the tag. The reading device 103 may then write into the database means, for example, that an image plate associated with a particular tag is faulty, whereby the X-ray device 102 can read the information associated with the ID of the tag from the database means during the imaging operation and detect and indicate that the image plate associated with the tag is faulty. Similarly, the X-ray device 102 may write into the database means information indicating the position of the image plate in the imaging operation so that the reading device 103 may later, having read the ID of the tag of the image plate, read the information concerning the position of the image plate in the imaging operation from the database means 107 and, based on that information, direct the image information to the correct location.

Reading information from a tag and writing to the tag can be implemented with short-range radio technology, for example. In addition it should be noted that in embodiments where only the ID of the tag is read, the tag may be implemented with a barcode or 2D barcode, for instance, in which case the reading of the tag can be done optically.

It should be noted that at least some of the means 103a to 103f may be integrated in the reading device or, alternatively, they may be separate from the reading device but operating together with it, e.g. means connected with the reading device through some communications link known to a person in the art.

Furthermore, in one embodiment, there is a means 102e in conjunction with the X-ray device 102 for writing information relating to the position of an image plate in the imaging operation into an image plate tag or into a database means in association with the ID of the tag. In one embodiment, the means 102e can be implemented e.g. by control keys or a computer or the like connected to the X-ray device, which can be used e.g. to select position information representing the position of the image plate from a menu.

In one embodiment, the means 102f of the X-ray device 102 is adapted to read, through the means 102b, from an image plate tag and/or database means an image plate imaging position information associated with the tag ID, e.g. in a situation in which a packing device or some other device or element has already generated a position for the image plate with respect to the imaging operation. Furthermore, the means 102f is adapted to indicate the image plate position information to the user through a display means, audible indications, and/or visible indications, for example.

In one embodiment, the reading means 102f in conjunction with the X-ray device 102 is adapted to read, through the means 102*b*, from an image plate tag, position information for the image plate with respect to the anatomy of the object examined when imaging position information for the image plate has been generated in the tag in advance, and if according to the position information read from the tag the image plate is incorrectly positioned in the imaging operation, the means 102*f* is adapted to indicate, through a display means, audible indications and/or visible indications, that the image plate is incorrectly positioned and/or the imaging operation is interrupted.

It should be noted that at least some of the means 102*a* to 102*f* in conjunction with the X-ray device may be integrated in the X-ray device or, alternatively, they may be separate from the X-ray device but operating together with it, e.g. means connected with the X-ray device through some communications link known to a person in the art. In addition it should be noted that at least some of the means 102*a* to 102*f* may constitute parts of an image plate holder 102*g* in the X-ray device.

The arrangement 100 may also include a means for interpreting and/or displaying the information delivered by the reading device 103, said means being e.g. a data processing means 108 in conjunction with the element 106 and being adapted to display, based on the information delivered by the reading device 103, the image information read from the image plates to the appropriate doctor or to be associated with the appropriate patient. The reading device 103 may e.g. deliver the image information and associated information relating to the patient or the doctor interpreting the images, whereby the data processing means 108 is adapted to display the appropriate image information e.g. to a doctor logged in on the data processing means 108. In one embodiment, the data processing means 108 is adapted to receive image information and associated position information and to attach or display said image information in the appropriate location on an image template representing e.g. the teeth of a patient, said appropriate location being that to which said image information related in the imaging operation according to the position information. In one embodiment, the above-described functions of the data processing means 108 can be implemented at least in part with a suitable computer software product.

In one embodiment, there is in conjunction with the image plate 104 an active tag 105*a* which could be a RFID tag, for example, during the imaging operation, and a direction sensor 109, the active tag being adapted to register the direction information produced by the direction sensor during the imaging. The direction sensor may e.g. provide information about how it is positioned in the vertical and/or lateral direction at the moment when it is hit by an X-ray or a RF beam. Then the tag may at a later stage also indicate the direction of the image plate during the imaging operation in association with any embodiment described in this document. Then it can be at a later stage ascertained how the image plate was positioned in the imaging operation, for example. It should be noted that even though a RFID tag is used here as an example, the embodiment can be implemented using other active tags as well, e.g. by means of other devices based on RF technology e.g. Bluetooth.

Furthermore, with respect to another embodiment of the invention, there may be at least two passive identifiers, e.g. RFID identifiers, in connection with an image plate which are arranged in the imaging operation in such a way that at least one passive RFID identifier is nearer to the RF read and/or write means of the X-ray device during the imaging operation than one other passive RFID identifier. For example, a first RFID identifier is nearer to the radiation-emitting X-ray tube and a second one is farther away, where the first and second identifiers are separated by an image plate and/or metal plate or some other means, for example. Then the direction of the image plate and the order of the identifiers can be determined e.g. as follows.

Instead of or in addition to active and passive tags, e.g. RFID identifiers, also semiactive tags, e.g. RFIDs, can be used in the image plate 104.

According to a first method, the RF reading means in the X-ray device reads the RF radiation emitted by both identifiers and based on the intensities of these two radiations determines which one of the identifiers emitting RF radiation is closer to the reading means and which one is farther away. The rays emitted by that RF radiator which is closer have a greater intensity than those of the one which is farther away. The difference of the intensities is especially large if RF-radiation-absorbing material, e.g. metal, is placed between the RF radiators. The metal element in that case may be located between the more distant RF radiator and the RF reading means of the X-ray device during the imaging operation.

In one embodiment, as regards the first method, the X-ray apparatus may be adapted to indicate in the manner described above if the image plate is positioned the wrong way round in the imaging operation, i.e. the first RF identifier, which should be closer to the RF reading means of the X-ray apparatus than the second RF identifier, is found to be farther away than the second RF identifier.

In one embodiment, the direction of an image plate can be determined also by means of one RF identifier. The RF identifier may be placed in the image plate in such a manner that on one side of the RF identifier there is material that absorbs RF radiation, a metal plate, for example. Then, for example during the imaging operation, the intensity of RF radiation emitted by said RF identifier can be measured and on the basis of the measured intensity it can be determined whether said RF-radiation-absorbing material is located between the RF identifier and the device that reads the RF radiation, especially when the intensity of RF radiation emitted by said RF identifier either without absorbing material and/or with absorbing material in between the RF identifier and the device reading RF radiation is known. Further, it is possible to determine whether the image plate is the right or wrong way round on the basis of whether or not said RF-radiation-absorbing material should be between the RF identifier and the device reading RF radiation during the imaging.

In one embodiment, the system, e.g an X-ray device or a device in connection therewith, may provide an indication, based on the determinings according to the above-described embodiments, for the fact that the image plate is the wrong way round. The indication may be done in some manner described in this document, for instance. Furthermore, the system may prevent the image plate from being exposed and/or prompt the user to turn the image plate around.

In a second method, the identifiers are adapted to indicate the degree of intensity of RF radiation that hit them in a situation where the RF reading means of the X-ray device is e.g. reading the RF identifier or writing into it or otherwise directs RF radiation on it, whereby at a later stage it is possible to determine, based on the intensity of the radiation received by the identifier, which identifier was closer and which one farther away. In this embodiment, the identifier which is closer will experience stronger RF radiation than the one farther away.

In one embodiment, the image plate can be equipped with an active tag and a radiation sensor adapted to sense the X-ray radiation hitting it. In that case the tag can automatically, without any special write operations, indicate that the image plate received X-rays and that the image plate has been exposed.

In one embodiment, the arrangement 100 or a device therein, e.g. a reading device 103 or data processing means in connection therewith may keep a record or statistics of image plates in the system and of their condition and may also be arranged to indicate to the user, through a display means, for example, when the number of faulty image plates exceeds a certain threshold value, and/or automatically place an order for additional image plates in a situation in which the number of faultless image plates drops below a certain threshold value.

In one embodiment of the invention, information about the health of the patient, e.g. a possible infectious disease, could be included in the arrangement 100, in the patient data and/or in the image plate tag. Said information about an infectious disease of a patient can be used for controlling the operation of the arrangement 100, e.g. by disallowing the interruption of the cleaning of an image plate containing an image of a patient indicated to have an infectious disease, e.g. in the reading device 103. Alternatively or in addition, the arrangement 100 may actuate an automatic cleaning of the reading device 103 after the reading of such an image, or the arrangement can be made such that it prompts the user to clean and/or replace e.g. components of the reading device 103, if it contains such components, following a patient associated with such infectious disease information.

FIG. 2 shows a template 200 for managing image plates 101 and image information contained in image plates and thereby controlling a medical imaging system in accordance with an embodiment of the invention. The template 200 comprises a place 201 for at least one image plate 101 and e.g. in intra-oral imaging, an individual place for each image plate used in the imaging of the teeth. The template 200 shown as an example in FIG. 2 comprises places 201 for all upper and lower teeth, front teeth, and posterior teeth.

In one embodiment, the places 201 on the template 200 are arranged so as to be identifiable, and they may be associated with an identifier, e.g. a positional identifier which identifies the particular place, e.g. FMX1, FMX2, . . . , FMX17, FMX18. Thus an image plate used at a certain place 201 of the template 200 in the imaging operation can at a later stage be associated with that particular place e.g. by writing the position identification of that place, e.g. FMX3, into the tag 105 attached to the image plate (or transport and/or protection means 104 of the image plate). Alternatively, said position identification can be written into a database means in such a manner that it can be associated with the ID of the tag, e.g. into the database means 107 shown in FIG. 1, from which place it can be later read, and by means of which the position of the image plate in the imaging operation can also be determined.

In one embodiment, the template 200 comprises a means 202 for delivering an identifier, e.g. a position identifier, relating to at least one place of the template, either to the tag attached to the image plate associated with that place or to a database means so that said image plate can at a later stage be associated with said place of the template. In one embodiment, each of the places on the template may comprise e.g. a RFID writing means 202r adapted to write the position identifier, e.g. FMX17, of the place of the template into a RFID tag attached to the image plate used on that particular place.

In another embodiment, the template 200 may comprise a means 203 for reading a tag attached to the image plate and for reading the ID of the tag. The template can then deliver to the database means the position information relating to the place of the image plate on the template together with the ID of the tag attached to the image plate so that the ID of the tag can at a later stage be associated with the template place.

In one embodiment, the template 200 may also read position information written into a tag of an image plate or position information which can be associated with the ID of said tag from a database means, where the position information relates to the place of the image plate on said template. Furthermore, the template 200 may comprise a means 204 adapted to compare the position information of an image plate to the place of the image plate on said template and, in addition, to indicate an incorrect location of an image plate on the template by means of audible and/or visible indications or using a display means integrated in the template or connected to it through a communications link, if the position information of said image plate does not match with the information indicating the place of the template where the image plate is located.

In one embodiment, the template is arranged to write also other information into the tag, or into a database means so that it can be associated with the ID of the tag, e.g. information related to the object or patient examined, or e.g. control information concerning the destination of the image information of the image plate, e.g. a file path or information specifying a certain doctor.

In addition, in one embodiment the template may comprise a means 205 for detecting a faulty image plate on the template on the basis of the image plate tag or based on information contained in a database means which information is associated with the ID of the tag. The means 205 is advantageously arranged to indicate the faultiness of an image plate e.g. as described in this document, e.g. using audible and/or visible indications or a display device.

In one embodiment, the above-mentioned functions of the template 200 can be controlled by e.g. a computer connected to the template, where the computer can be used e.g. to write to the tag of an image plate placed on the template information about the location of the image plate on the template. The computer may also be used to read information from tags of image plates placed on locations of the template. When using a computer or a similar device to control the template it is obvious that the template 200 then comprises a read and/or write means for reading from and writing to the tag, as well as a means for communicating with the device used for controlling the template.

It should be noted that in one embodiment the position information can be written to the tag and/or database means also manually in connection with imaging.

FIG. 3 shows a packing means 300 for providing image plates 101 with an image plate transport and/or protection means 104 and thereby for controlling a medical imaging system in accordance with an embodiment of the invention. The packing means 300 comprises in one embodiment a means 301 for reading a tag associated with an image plate or with a transport and/or protection means intended for a tag, and/or a means 302 for writing to the tag. Alternatively, the means 301 and 302 may be adapted to read the ID of the tag and write and/or read information associated with the tag to or from a database means.

In one embodiment, the packing means is adapted to read position information relating to the position of an image plate in the imaging operation, where the position information indicates the position of the image plate with respect to the anatomy of the object examined, other image plates used in the imaging, and/or imaging equipment. The packing means may read the position information through the means 301 e.g. from a tag attached to the image plate or from a database means utilizing the ID of the tag.

The packing means may also comprise a means 303 for printing out the position information of the image plate onto the image plate or its transport and/or protection means.

In one embodiment, the packing means comprises a means 304 for generating position information e.g. in a series of multiple image plates, whereby the packing means may be adapted to write the position information which it has generated e.g. to an image plate tag and/or database means where it can associated with the ID of the tag. The packing means may also be controlled by a data processing device communicating with the packing means, whereby the data processing device may generate said position information and deliver it to the packing means which in turn may be adapted to write and print out said information e.g. in the manner described above.

In one embodiment, the packing means comprises a means 305 for taking an image plate out of use if information in a tag read by the reading means 301 indicates that the image plate associated with the tag is faulty. A packing means according to an embodiment, where the packing means is adapted to get from an image plate tag or from information associated with the image plate through database means, information about the condition of the image plate, and to take the image plate out of use if said information about the condition of the image plate indicates that the image plate is faulty.

The packing means may read the tag and/or write to the tag using short-range radio technology, for instance. In addition it should be noted that in embodiments where only the ID of the tag is read, the tag may be implemented with a barcode or 2D barcode, for instance, in which case the reading of the tag can be done optically.

Only a few embodiments of the solution according to the invention were described above. The principle according to the invention, as regards e.g. implementation details and field of application, may naturally be modified within the scope of the invention defined by the claims. Especially it should be noted that even though in many of the embodiments described above there was given an example where the control information is read from the tag and/or written to the tag, the embodiment may also be implemented such that control information related to the ID of the tag is read from a database means and/or control information is written to a database means in association with the ID of the tag. It should also be noted that even though it was above said that the tag is associated with an image plate, the tag may be attached either directly on the image plate or, alternatively, on a transport and/or protection means associated with the image plate.

It should further be noted that also other information than that which has been mentioned in this document, e.g. information for controlling the arrangement, can be written to the tag or to a database means in association the with ID of the tag. Indeed one object of the present invention is to use said information for controlling the arrangement or its component devices. Also other kinds of information can be written, e.g. Dicom information comprising information related to the referral, doctor, patient, and/or imaging operation.

Furthermore, it should be noted that the above-described functions relating to the arrangement, e.g. reading device, X-ray source, template, and/or packing means, can be implemented, at least in part, using suitable computer software.

It should also be noted that the present invention can be applied in systems used for intra-oral imaging, for example, but also in other medical X-ray imaging techniques in which image plates are used, regardless of e.g. the size of the image plate used or the protection means used in conjunction therewith.

The invention claimed is:

1. An arrangement for medical X-ray imaging comprising:
   an image plate for use in intraoral imaging, wherein an X-ray image of an object examined is producable on the image plate, the X-ray image producable on the image plate being readable by a reading device;
   a tag attached to the image plate, and the tag contains information for controlling the arrangement for medical X-ray imaging in such manner that, when the arrangement has read the information in the tag, the arrangement is configured to perform at least one operation controlled by the information in the tag;
   reading and writing means for remotely reading from the tag and for remotely writing to the tag;
   wherein the information in the tag comprises position information that indicates a position of the image plate with respect to teeth of a patient and the at least one operation comprises that the reading device delivers the X-ray image and the position information to a data processing means and the data processing means attach the X-ray image in an appropriate location on an image template representing the teeth of the patient; and
   wherein the appropriate location is that to which the X-ray image relates according to the position information.

2. The arrangement according to claim 1, wherein the tag comprises information for controlling the arrangement so that when the reading device has read the image information contained in the image plate, the arrangement is configured to deliver said image information to a place indicated by the information read from the tag to a party that took or will interpret the image so that said image information is associated with a person involved in the imaging.

3. The arrangement according to claim 2, wherein the reading device is configured to analyze the condition of the image plate and write to the tag information related to the condition of the image plate, which information indicates that the image plate is faulty.

4. The arrangement according to claim 1, wherein said tag contains exposure information indicating that the image plate contains image information, whereby the arrangement is configured, based on the reading of said exposure information, to activate the reading device.

5. The arrangement according to claim 4, wherein the arrangement is configured, having read or reset the image information, to alter the exposure information in the tag to indicate that the image information has been read or said image plate does not contain image information.

6. The arrangement according to claim 5, wherein the reading device is configured to analyze the condition of the image plate and write to the tag information related to the condition of the image plate, which information indicates that the image plate is faulty.

7. The arrangement according to claim 4, wherein the reading device is configured to analyze the condition of the image plate and write to the tag information related to the condition of the image plate, which information indicates that the image plate is faulty.

8. The arrangement according to claim 1, wherein the reading device is configured to analyze the condition of the image plate and write to the tag information related to the condition of the image plate, which information indicates that the image plate is faulty.

9. An arrangement for medical X-ray imaging, comprising:
   an image plate for use in intraoral imaging, the image plate configured to produce thereon an X-ray image of an object examined;
   a tag attached to the image plate, and the tag contains information for controlling the arrangement for medical X-ray imaging;
   a reading device operable to read the X-ray image of the object examined from the image plate, the reading device operable to remotely read from the tag and remotely write to the tag the information for controlling the arrangement for medical X-ray imaging, the information for controlling comprising at least position information that indicates a position of the image plate with respect to teeth of a patient;
   a template representing the teeth of the patient; and
   a computer that receives the position information read by the reading device and the computer receives the X-ray image of the object examined from the reading device and the computer attaches the X-ray image of the object examined in an appropriate location on the image template, being that to which the X-ray image relates according to the position information.

10. The arrangement according to claim 9, wherein the tag comprises information for controlling the arrangement so that when the reading device has read the X-ray image contained in the image plate, the arrangement is configured to deliver said X-ray image to a place indicated by the information read from the tag to a party that took or will interpret the image so that said image information is associated with a person involved in the imaging.

11. The arrangement according to claim 10, wherein the reading device analyzes the condition of the image plate and writes to the tag information related to the condition of the image plate.

12. The arrangement according to claim 9, wherein the tag contains exposure information indicating that the image plate contains image information, whereby the arrangement is configured, based on the reading of said exposure information, to activate the reading device.

13. The arrangement according to claim 12, wherein the arrangement is configured, having read or reset the image information, to alter the exposure information in the tag to indicate that the image information has been read or said image plate does not contain image information.

14. The arrangement according to claim 13, wherein the reading device is configured to analyze the condition of the image plate and write to the tag information related to the condition of the image plate.

15. The arrangement according to claim 12, wherein the reading device is configured to analyze the condition of the image plate and write to the tag information related to the condition of the image plate.

16. The arrangement according to claim 9, wherein the reading device is configured to analyze the condition of the image plate and write to the tag information related to the condition of the image plate.

17. An arrangement for medical X-ray imaging comprising:
   an image plate; and
   reading and writing means for remotely reading from a tag and for remotely writing to the tag;
   wherein an X-ray image of an object examined is producible on the image plate,
   wherein image information contained in the image plate readable by a reading device,
   wherein the tag is attached to the image plate,
   wherein the image plate usable in intraoral imaging, and
   wherein said tag contains information for controlling the arrangement in such manner that, when the arrangement has read the information in the tag, the arrangement is configured to perform at least one operation controlled by said information read,
   wherein the information in the tag comprises position information that indicates a position of the image plate with respect to teeth of a patient and
   wherein the at least one operation comprises that the reading device delivers said image information and the position information to data processing means and the data processing means attach the image information in an appropriate location on an image template representing the teeth of the patient, wherein said appropriate location is that to which said image information relates according to the position information.

18. The arrangement according to claim 17, wherein the tag comprises information for controlling the arrangement so that when the reading device has read the image information contained in the image plate, the arrangement is adapted to deliver said image information to a place indicated by the information read from the tag to a party that took or will interpret the image so that said image information is associated with a person involved in the imaging.

19. The arrangement according to claim 17, wherein the reading device is configured to analyze the condition of the image plate and write to the tag information related to the condition of the image plate, which information indicates that the image plate is faulty.

20. The arrangement according to claim 17, wherein said tag contains exposure information indicating that the image plate contains image information, whereby the arrangement is configured, based on the reading of said exposure information, to activate the reading device.

* * * * *